United States Patent [19]

Zara et al.

[11] Patent Number: 5,157,123

[45] Date of Patent: Oct. 20, 1992

[54] S-(2-THIOPYRIDYL)-L-CYSTEINE, A HETEROBIFUNCTIONAL CROSSLINKING REAGENT

[75] Inventors: Jane J. Zara; Richard D. Wood; Reinhard Bredehorst; Carl-Wilhelm Vogel, all of Washington, D.C.

[73] Assignee: Georgetown University, Washington, D.C.

[21] Appl. No.: 322,214

[22] Filed: Mar. 13, 1989

[51] Int. Cl.$^5$ ................. C07D 213/62; C07D 213/52; C07D 213/127; C07C 229/02
[52] U.S. Cl. ................... 546/291; 562/553; 562/561; 546/294; 436/547
[58] Field of Search ............... 546/291, 294; 424/85.91; 436/547, 548; 536/1.1, 56, 102, 114; 530/395; 562/553, 561

[56] References Cited

U.S. PATENT DOCUMENTS

| | | | |
|---|---|---|---|
| 4,489,710 | 12/1984 | Spitler et al. | 424/85 |
| 4,671,958 | 6/1987 | Rodwell et al. | 424/85 |
| 4,797,491 | 1/1989 | Nitecki et al. | 546/291 |
| 4,880,935 | 11/1989 | Thorpe | 546/281 |
| 4,994,385 | 2/1991 | Bieniarz et al. | 436/547 |

FOREIGN PATENT DOCUMENTS 63-57569  1/1988  Japan.
87-06837  7/1987  PCT Int'l Appl..

OTHER PUBLICATIONS

Chemical Abstracts: 95:57582g, 1981, Chong et al. J. Biol. Chem. 256(10): 5064-70, 1981.
Chemical Abstracts: 94:135401t 1981, Taylor et al. BIochem. Int. 1(4) 353-8, 1980.
Sigma Chemical Company Catalog, 1990, p. 234.
Lange's Handbook of Chemistry, John A. Dean, Editor, Thirteen Edition, 1972, (McGraw-Hill Co.: New York), pp. 7-501 and 7-687.
Shriner et al. The Systematic Identification of Organic Compounds, Fifth Edition, 1964, (John Wiley & Sons; New York, pp. 72-87.
Sela et al, *Immunoconjugates. Antibody Conjugates in Radioimaging and Therapy of Cancer*, pp. 189-216 Oxford Univ. Press (1987).
O'Shannessy, *Int. So. Biorecognition Tech.*, vol. 3, pp. 4-6 (1988).
*Biochem. J.*, vol. 173, p. 723 (1978).
Streitwieser et al., "Introduction to organic Chemistry", Macmillan, pp. 168-169 (1985).
*Hackh's Chemical Dictionary*, McGraw-Hill, pp. 303, 437 and 465 (1969).
Stryer, "Biochemistry", W. H. Freeman, p. 287 (1988).

Primary Examiner—Johnnie R. Brown
Assistant Examiner—Gary L. Kunz
Attorney, Agent, or Firm—Oblon, Spivak, McClelland, Maier & Neustadt

[57] ABSTRACT

Site-specific heterobifunctional crosslinkers of the formula:

$$X-COCH(NH_2)-Y-Z$$

where X is a carbonyl reactive group, Y is a variable length spacer, and Z is a thiol reactive group, are useful for the specific labelling of biomolecules or bioaffecting molecules.

1 Claim, 2 Drawing Sheets

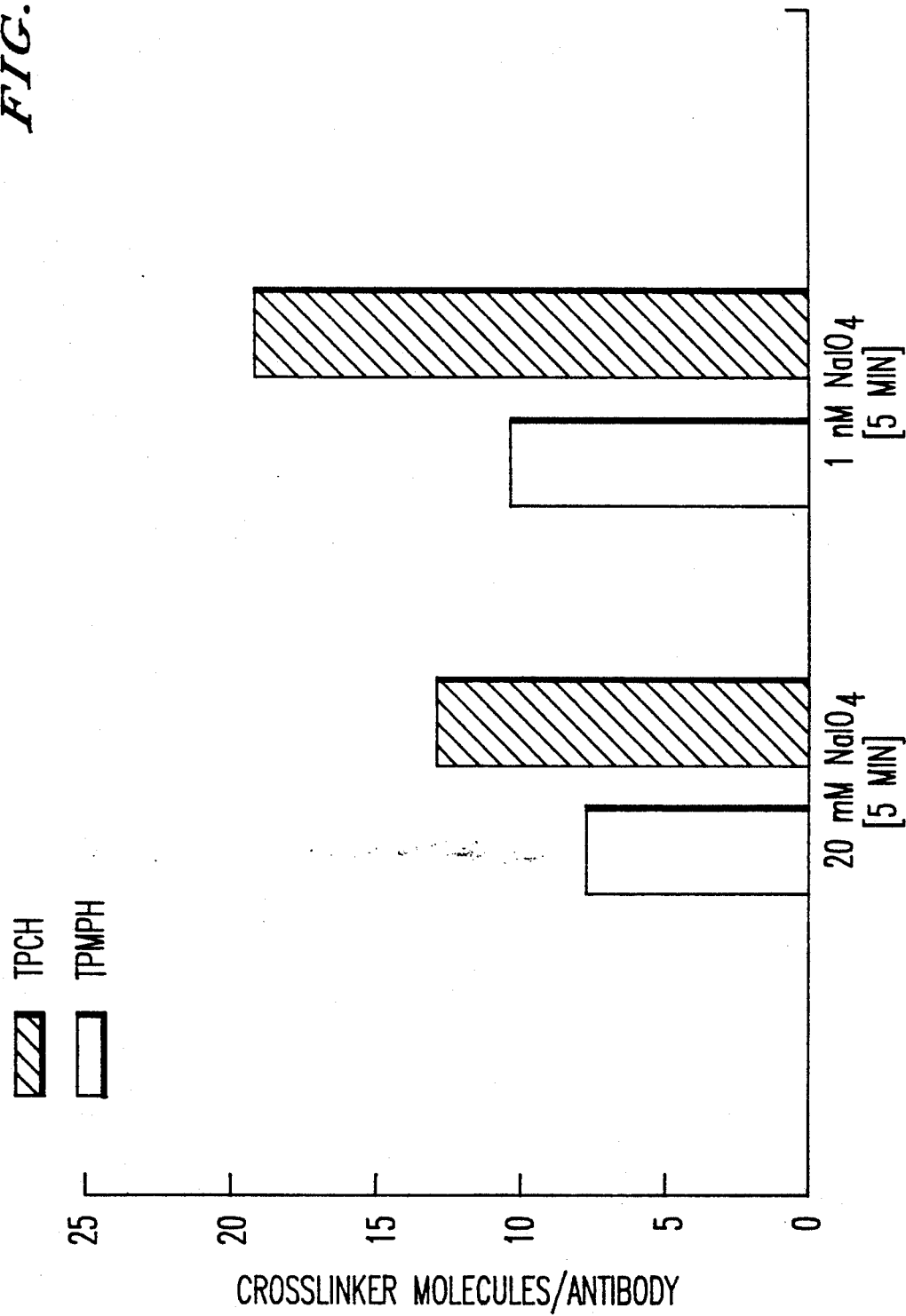

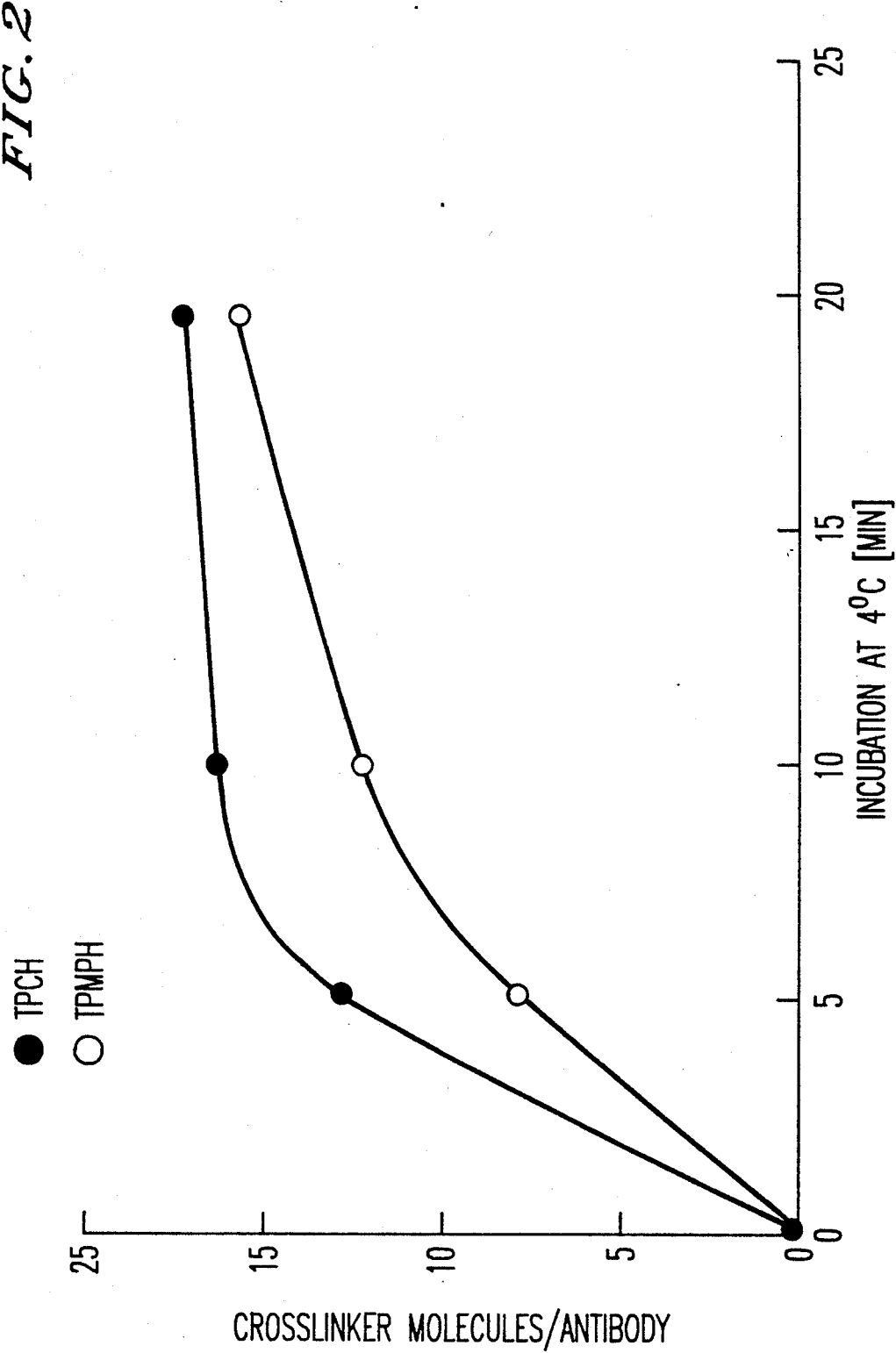

S-(2-THIOPYRIDYL)-L-CYSTEINE, A HETEROBIFUNCTIONAL CROSSLINKING REAGENT

BACKGROUND OF THE INVENTION

1. Field of the Invention

The present invention relates to site-specific heterobifunctional crosslinking reagents, biomolecules or bioaffecting molecules to which the present crosslinking reagents are bound, and kits containing biomolecules or bioaffecting molecules to which the present crosslinking reagents are bound.

2. Discussion of the Background

Heterobifunctional crosslinking reagents are widely used for linking effector molecules to biomolecules such as glycoproteins including antibodies, lectins, enzymes, and response modifiers.

In particular, immunoconjugates result from the chemical coupling of monoclonal antibodies with various effector molecules, which may include toxins (e.g., ricin A chain; reviewed by Moller, in, *Immunol. Rev.*, p. 62, Copenhagen (1982)), biological response modifiers (e.g., cobra venom factor; reviewed by Vogel in *Immunoconjugates. Antibody Conjugates in Radioimaging and Therapy of Cancer*, pp. 170–188 Oxford Univ. Press 1987)), and low molecular weight drugs (e.g., doxorubicin; reviewed by Sela and Hurwitz in *Immunoconjugates. Antibody Conjugates in Radioimaging and Therapy of Cancer*, pp. 189–216, Oxford Univ. Press (1987)). The potential of such immunoconjugates for the development of novel anti-cancer therapeutics and imaging techniques has been studied by many investigators and has been reviewed by C.-W. Vogel in *Immunoconjugates*, Oxford Press (1987), Several methods for coupling effector molecules to monoclonal antibodies are known. Currently used methods for the synthesis of immunoconjugates employ heterobifunctional crosslinking reagents which contain one amino-reactive residue (e.g., succinimidyl ester) and one sulfhydryl-reactive residue (e.g., pyridyl disulfide). An example of such heterobifunctional reagents is N-succinimidyl-3-(2-pyridylthio)propionate (SPDP) which is described in *Biochem. J.*, vol. 173, pp. 723–737 (1978). Upon incubation of antibodies with SPDP, the crosslinking reagent is coupled via an amide bound to one of the primary amino groups of the antibody, thereby introducing a pyridyl disulfide moiety to which a sulfhydryl-containing effector molecule can be coupled.

One major problem of this technique, however, is the random distribution of amino groups throughout the entire antibody molecule including the antigen binding region. Thus, the crosslinking agents may bind to the antibody at a site close to the binding region of the antibody and, thus, interfere with the binding of the antibody. Therefore, use of the currently available heterobifunctional crosslinking agents diminishes the antigen binding capability of the resulting immunoconjugates and, thereby, limits their efficacy as therapeutic and diagnostic agents.

More recently, the reaction of amine-containing molecules with the carbohydrate region of antibodies has been investigated for the purpose of preparing antibody derivatives, see D. J. O'Shannessy, *Int. Soc. Biorecognition Tech.*, vol. 3, pp. 4–6 (1988).

PCT Patent Application WO87/06837 discloses linking amine-derivatives of folic acid to antibodies which contain an oxidized carbohydrate moiety.

U.S. Pat. No. 4,671,958 discloses the use of crosslinkers, one end of which contains a hydrazine derivative, for the purpose of reacting with oxidized antibody carbohydrate moieties. However, only enzymatically cleavable crosslinkers are disclosed.

Japanese Patent Application J63-57569 discloses bridging agents which are hydrazide compounds of the formula X—SS-A-CONHNH$_2$, where X is 2-pyridyl or 4-pyridyl and A is a C$_1$ to C$_6$ divalent hydrocarbon group (e.g., —CH$_2$CH$_2$—, —CH$_2$CH$_2$CH$_2$—). These compounds are used to link effector molecules to the sugar chain of an antibody. For example, the antitumor agent methotrexate is linked to an antitumor antibody via the sugar chain to give an antibody/methotrexate complex to be used in target therapy. Linking enzymes with antibodies for enzyme immunoassays is also disclosed.

However, the crosslinkers of J63-57569 react relatively slowly with biomolecules so that they require the antibody to be exposed to the oxidizing medium for a prolonged period of time. The prolonged exposure of the antibody leads to undesirable side reactions which decrease the binding function of the antibody. Further, the crosslinkers of J63-57569 are not sufficiently water soluble to make their handling and manipulation easy.

In addition, the crosslinkers of J63-57569 are achiral and, thus, the possibility of optical isomers does not exist. Since many of the molecules which are to be attached to crosslinkers exist as optically pure isomers, crosslinkers which can exist as optical isomers might possess some advantages, such as site specificity.

Thus, there remains a need for site-specific heterobifunctional crosslinkers which couple to biomolecules or bioaffecting molecules with a high efficiency, react with biomolecules and bioaffecting molecules with a high rate, and possess a high water solubility.

SUMMARY OF THE INVENTION

It is an object of the present invention to provide site-specific heterobifunctional crosslinkers which couple with biomolecules and bioaffecting molecules with a high efficiency.

It is another object of the present invention to provide site-specific heterobifunctional crosslinkers which react with biomolecules and bioaffecting molecules at a high rate.

It is another object of the present invention to provide site-specific heterobifunctional crosslinkers which possess a high water solubility.

It is another object of the present invention to provide biomolecules and bioaffecting molecules to which the present site-specific heterobifunctional crosslinkers have been attached.

It is another object of the present invention to provide kits which contain biomolecules or bioaffecting molecules to which the present site-specific heterobifunctional crosslinking agents have been attached.

These and other objects of the present invention which will become apparent during the course of the following detailed description have been achieved by crosslinking agents having the formula:

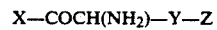

X—COCH(NH$_2$)—Y—Z wherein X is $H_2NNH-$, $H_2NNHCONHNH-$, $H_2NNHCONH-$, $H_2NO(CH_2)_nNH-$, $H_2NOCO(CH_2)_nNH-$, or $H_2N(CH_2)_nNH-$, where n is an integer of 2 to 6; Y is a divalent group having 1 to 20 carbon atoms, which may be interrupted by heteroatoms, and may be substituted with hydroxyl, carboxy, sulfonate, phosphonate, and quaternary ammonium groups; and Z is dithiopyridyl, thiolacetate, or maleimide.

BRIEF DESCRIPTION OF THE DRAWINGS

A more complete appreciation of the present invention and many of the attendant advantages thereof will be readily obtained as the same become better understood by reference to the following detailed description when considered in connection with the accompanying drawings, wherein:

FIG. 1 shows a comparison for the incorporation of TPCH versus TPMPH into human monoclonal IgM antibody 688; and FIG. 2 compares the kinetics of incorporation of TPCH and TPMP into human monoclonal IgM antibody 1688.

DETAILED DESCRIPTION OF THE PREFERRED EMBODIMENTS

The present invention relates to site-specific heterobifunctional crosslinkers having the formula:

$$X-COCH(NH_2)-Y-Z$$

where X may be $H_2NNH-$, $H_2NNHCONHNH-$, $H_2NNHCONH-$, $H_2NO(CH_2)_nNH-$, $H_2NOCO(CH_2)_nNH-$, or $H_2N(CH_2)_nNH-$, where n is an integer of 2 to 6.

Y is a divalent group having 1 to 20 carbon atoms, which may be interrupted by heteroatoms, and which may be substituted by hydroxyl, carboxy, sulfonate, phosphonate, and/or quaternary ammonium groups. The purpose of the spacer region Y is to separate the reactive groups X and Z of the linker. This region may vary in length between one and twenty carbon atoms. In a preferred embodiment, Y is a $C_1$-$C_3$ alkylene moiety. When Y is interrupted by heteroatoms, it is preferably interrupted by 1 to 3 atoms selected from: O, N, and S.

The $C_1$-$C_{20}$ divalent organic group for Y may also be substituted by 1-5 functional groups. One reason for this substitution is to impart greater hydrophilicity to the overall molecule. Thus, as the carbon atom content increases, the number of substituents is desirably increased in order to adjust the aqueous solubility of the molecule. Suitable functional groups include hydroxyl, carboxylate, sulfonate, phosphonate, and quaternary ammonium salts. These functionalities can all be introduced by conventional methods, e.g., via reductive amination of keto residues. The quaternary ammonium salts are preferably of the formula $-NR_1R_2R_3.X^-$, wherein each of $R_1$ to $R_3$ is independently selected from $C_1$-$C_7$ alkyl or hydrogen, and X is an anion such as chloride, bromide, etc.

In one embodiment, the ends of the Y region precursor may be carboxylic acid residues, to facilitate the coupling to the amino acid and Z regions of the linker. A number of diacids containing keto functionalities are available and may be used as convenient precursors to the Y region. For example, sulfonate, phosphonate, or pyridinium residues can be introduced into 4-ketopimelic acid by treatment of the ketone with an appropriate amine under reducing conditions:

$$(HOOCCH_2CH_2)_2CO + H_2NCH_2CH_2R \longrightarrow$$

$$(HOOCCH_2CH_2)CNHCH_2CH_2R$$

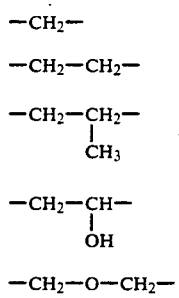

where R = $SO_3^-$, $OP_3^-$, $-\overset{+}{N}\bigcirc$

Examples of Y-region precursors which contain a carbon chain interrupted by heteroatoms include those derived from poly(alkylene oxides), such as poly(ethylene oxide), poly(propylene oxide), and poly(butylene oxide) and poly(alkylene imines), such as poly(ethylene imine), poly(propylene imine) and poly(butylene imine). Among these, poly(ethylene oxide) and poly(ethylene imine) are preferred due to hydrophilicity considerations.

Specific examples of Y-region precursors which contain carbon chains interrupted by heteroatoms include:

$HO_2CCH_2O(CH_2CH_2O)_nCH_2CO_2H$, where n=0 to 8;

$HO_2CCH_2CH_2O(CH_2CH_2CH_2O)_nCH_2CH_2CO_2H$, where n=0 to 4;

$HO_2CCH_2N(CH_2CH_2N)_nCH_2CO_2H$, where n=0 to 8; and $HO_2CCH_2CH_2N(CH_2CH_2CH_2N)_nCH_2CH_2CO_2H$, where n=0 to 4.

The following are some additional specific Y groups which are contemplated:

$-CH_2-$ $-CH_2-CH_2-$ $-CH_2-\underset{CH_3}{\overset{|}{C}H}-$ $-CH_2-\underset{OH}{\overset{|}{C}H}-$ $-CH_2-O-CH_2-$ Each of the molecules of the present invention can exist as enantiomers due to the chiral carbon to which the α-amino group is attached. Both D and L isomers, as well as mixtures of the two (e.g., a racemic mixture) are contemplated as part of this invention. The optically active molecules may be prepared by resolving mixtures thereof or may be prepared from optically active precursors. The L isomers are preferred. When the substituted Y groups are capable of optical activity, additional isomers will be possible, and these are also part of the present invention, both individually and as a mixture.

The functional group of the Z segment serves to bind a second biomolecule or bioaffecting molecule to the crosslinker. The reactive group of the Z region is preferably: 2-dithiopyridyl, 4-dithiopyridyl, thiolacetate, or maleimide. Each of these Z groups is preferably unsubstituted, but could be substituted by 1 to 3, preferably 1, substituent selected from: halogen (e.g. Cl, Br, I, F), nitro, hydroxy, and $C_{1-4}$ alkyl In the case of dithiopyridyl, a stable disulfide bond will be formed between the present crosslinkers and a thiol appended from the molecule to which it is linked. The thiolacetate functionality permits the introduction of a masked thiol into the carrier-linker adduct. Liberation of the acetate group, e.g., via reduction or base-catalyzed hydroylsis provides a free mercaptan which can then form a stable linkage with a molecule which contains a thiol reactive group, such as, e.g., dithiopyridyl or maleimide functionalities. The maleimide group permits the formation of a stable sulfide upon reaction with a molecule bearing a mercaptan.

The compounds of the present invention can exist as salts. These salts also form part of the present invention. The salt of the α-amino group may be any conventional salt known to an organic chemist. Preferred salts are: hydrochloride, hydrobromide, p-TsOH, hydroiodide, etc.

In a preferred embodiment Y is $-CH_2-$, because then the present crosslinkers may be directly prepared by linking the X and Z units to cysteine. $NH_2NH-$ is preferred for X, and dithiopyridyl is preferred for Z. The compound, wherein Y is $-CH_2-$, X is $NH_2NH-$ and Z is 2-dithiopyridyl, is S-(2-thiopyridyl)-cysteine hydrazide, referred to herein as TPCH, and is a particularly preferred embodiment. It can exist as D and L isomers, and the L is preferred. It can also exist as a salt, and the trihydrochloride is preferred. The synthesis of this compound is discussed hereinbelow.

Synthesis

The present crosslinkers may be synthesized via coupling of an amine-containing compound, such as $H_2NNH_2$, $H_2NNHCONHNH_2$, $H_2NNHCONH_2$, $H_2NO(CH_2)_nNH_2$, $H_2NOCO(CH_2)_nNH_2$, or $H_2N(CH_2)_nNH_2$ with a carboxylic acid. The carboxylic acid may be derived from an amino acid precursor. The amino acid precursor may be N-protected, and the amine-containing compound may be protected at one of the $-NH_2$ groups. Suitable N-protecting groups include, e.g., t-butyloxycarbonyl (t-BOC), carbobenzoxy (CBZ), 9-fluorenylmethoxycarbonyl (FMOC), o-nitrophenylsulfenyl, or p-nitro-2-pyridinesulfenyl. t-BOC is preferred.

The carboxyl group of the amino acid precursor may be derivatized to form a more reactive group, such as, e.g., an acyl halide, in particular an acyl chloride.

The coupling of the amino acid precursor and the amine-containing compound may be mediated by a dehydrating agent, such as, a carbodiimide, in particular N,N'-dicyclohexylcarbodiimide (DCC). An example of one coupling reaction is shown below:

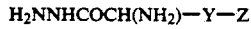

In the case where X is $H_2NO(CH_2)NH-$, the synthesis of the X region precursor may be accomplished by the alkylation of a N-hydroxycarbamate, such as, e.g., t-butyl-N-hydroxycarbamate, with a reagent having the structure $L(CH_2)_nNH_2$, where L is a leaving group and the $-NH_2$ group may be protected. Suitable leaving groups include, e.g., the halides, and iodide is preferred. Suitable $-NH_2$ protecting groups are those given above, and again, t-BOC is preferred. An example of one preparation of one X-region precursor from a reagent prepared from γ-aminobutyric acid is shown below:

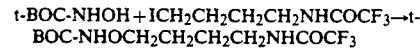

In this case, the trifluoroacetamide protection can be selectively cleaved by conventional methods and the resulting free amino group coupled with an amino acid optionally containing the Y and Z linker segments, as described above.

When X is $H_2NOCO(CH_2)_nNH-$, the precursor for the X region may be prepared by the acylation of a N-hydroxycarbamate, such as, e.g., t-butyl-N-hydroxycarbamate, with a reagent having the structure $L'CO(CH_2)_nNH_2$, where L' is a group such as $-OH$ or a halide and the $-NH_2$ group may be protected as described above. When L' is $-OH$ the reaction may be mediated with a dehydrating agent as described above. An example of one preparation of one X-region precursor from a reagent prepared from Y-aminobutyric acid is shown below:

Again, the trifluoroacetamide protection can be removed and the free amino group coupled with an amino acid.

When X is $H_2N(CH_2)_nNH-$, the crosslinkers can be prepared by the reaction of the amino acid, which may or may not contain linker sections Y and Z, with a diamine. The diamine may be partially protected with any of the above-mentioned protecting groups, preferably t-BOC, and the coupling may be mediated by any of the above-mentioned dehydrating agents, preferably DCC.

One example of one coupling reaction is shown below:

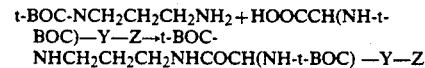

In all of the above cases, the amine protecting groups can be removed as a final step. For example, the t-BOC protection can be removed as a final step by treatment with anhydrous HCl or trifluoroacetic acid.

The coupling of the segments of the linker follows conventional methodology and may vary with the incorporation of some of the options outlined above. A preferred central building block for the linker is cysteine, which provides not only the crucial α-amine but a reactive sulfhydryl group. For example, the above-mentioned diacid precursors for the Y region can be reduced and halogenated selectively at one end, and the resulting active halo compound can be used to alkylate the thiol of cysteine, which is optionally protected at the amine and carboxyl groups. The second carboxylic acid function of a diacid Y-region precursor may also be protected. Suitable amine protecting groups are those mentioned above, with t-BOC being preferred. Suitable carboxy protecting groups include, e.g., benzyl ester, t-butyl ester, ethyl ester, and methyl ester.

Deprotection of the cysteine-derived carboxy and coupling with any of the groups enumerated under the discussion of X given above may be effected as discussed above.

The X-amino acid-Y conjugate may then be coupled with reagents containing the Z functionalities discussed above. The free carboxy functionality of Y may be transformed into a more nucleophilic and hydrophilic residue, such as an acyl hydrazide, e.g., via carbodiimide-mediated coupling with carbohydrazide. Subsequent reaction with any of several conventional reagents, e.g., SPDP, will introduce the Z portion of the linker. A final deprotection step may be necessary.

Preferably, the X, Y and Z groups are selected so that they are not readily chemically reactive among each other. Dithiopyridyl is unreactive toward and thus compatible with all X regions. Thiolacetate is compatible with $H_2NO(CH_2)_nNH-$ and $H_2NO-CO(CH_2)_nNH-$ at pH up to 4 and with $H_2N(CH_2)_nNH-$ at a pH from about 4 to about 7. Maleimide is compatible with all of the X regions in the pH ranges at which the X regions are substantially protonated.

S-(2-thiopyridyl)-L-cysteine hydrazide (TPCH) is the particularly preferred crosslinker. One synthesis of TPCH is outlined below.

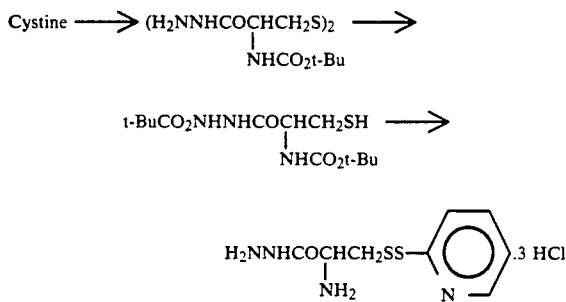

L-Cystine alkyl ester dihydrochloride can be prepared from commercially available L-cystine (Aldrich Chemical Co.) by treatment with thionyl chloride in an alcohol. The amino ester may be protected with ditert-butyl dicarbonate, affording the bis(tert-butyl urethane) derivative. The corresponding bis(hydrazide) may be prepared by treatment with excess hydrazine and may be protected at the hydrazide functionality by reaction with di-tert-butyl dicarbonate. The disulfide linkage can be reductively cleaved with, e.g., zinc dust in aqueous acetic acid, providing the free thiol. The dithiopyridyl functionality may be introduced by reaction with 2,2'-dipyridyl disulfide. Finally the removal of the two urethane groups provides TPCH as a hygroscopic white crystalline powder.

Uses of the Crosslinkers invention may be used to couple a variety of compounds.

It is preferred that the present crosslinkers are coupled via the X region to biomolecules and bioaffecting molecules which contain an amine reactive group or a group which can be converted to an amine reactive group, such as a carbohydrate group. By "biomolecules" and "bioaffecting molecules" is meant glycoproteins, glycolipids, nucleic acids, monosaccharides, and polysaccharides and drugs. Glycoproteins include antibodies, lectins, enzymes, and response modifiers.

For example, the present X groups can react with a number of different functional groups including aldehydes, hemiacetals, ketones, and carboxy groups. When the present crosslinkers are coupled to carboxy groups via X, the coupling reaction may be mediated by a dehydrating agent, such as a carbodiimide.

Examples of compounds which may be derivatized via aldehyde functions include glycoproteins (see, e.g., Debray et al., *J. Biol. Chem.*, vol. 250, 1955 (1975) and Bayer et al., *Methods Biochem. Anal.*, vol. 26, 1 (1980)), such as antibodies (e.g., IgM; O'Shannessy, *Int. Soc. Biorecognition Tech.*, vol. 3, pp. 4-6 (1988) and IgG; Rodwell et al., *Proc. Natl. Acad. Sci. USA*, vol. 83, pp. 2632-2636 (1986)), lectins (e.g., ricin; Montfort, et al., *J. Biol. Chem.*, vol. 262, pp. 5398-5403 (1987)), enzymes (e.g., alkaline phosphatase; Fosset, et al., *Biochem.*, vol. 13, pp. 1783-1788 (1974)) and response modifiers (e.g., cobra venom factor; Vogel, et al., *J. Immunol. Meth.*, vol. 73, pp. 203-220 (1984)); glycolipids, e.g., cerebroside; nucleic acids, e.g., RNA; mono- or polysaccharides, e.g., gangliosides (Spiegel et al., *Biochem. Biophys. Acta*, vol. 687, 27 (1982)); and drugs, e.g., doxorubicin.

Examples of compounds which may be derivatized via a hemiacetal group include mono- or polysaccharides, such as oligosaccharides with a reducing terminus. The derivatization of doxorubicin via the C-13 keto group has been reported in *Annals of the New York Academy of Sciences*, volume 417, pp. 125-136 (1983). Compounds which may be derivatized via the carbodiimide-mediated reaction of a carboxy group include drugs such as succinylated T2-toxin.

The present crosslinkers may be coupled to molecules via the X-region by any of the conventional methods, such as those described in O'Shannessy, *Int. Soc. Biorecognition Tech. Commun.*, vol. 3, pp. 4-6 (1988), which is incorporated herein by reference. For example, the present crosslinkers may be coupled to the oxidized carbohydrate region of an antibody. The carbohydrate region of antibody may be oxidized by any conventional oxidant such as periodate, periodic acid, para-periodic acid, or metaperiodate. In addition, enzymatic oxidation with, e.g., galactosidase as described in *Biochem. Biophys. Acta*, vol. 800, pp. 291-300 (1984), is also suitable.

The present crosslinkers may be coupled to the oxidized carbohydrate region of an antibody by first oxidizing the carbohydrate region and then reacting the oxidized antibody with the crosslinker. Alternatively, the coupling may be accomplished by oxidizing the antibody in the presence of the present crosslinker. The latter method results in fewer undesirable side reactions which can decrease the binding function of the antibody and, thus, is preferred.

The product of the coupling of the present crosslinkers with either a carbonyl or hemiacetal group of a biomolecule may be represented by the formula:

in which X' is $=NNH-$, $=NNHCONHNH-$, $=NNHCONH-$, $=NO(CH_2)_nNH-$, $=NO-CO(CH_2)_nNH-$, and $=N(CH_2)_nNH-$, where n is an integer of 2 to 6, Y and Z are defined as above, and B is a biomolecule or bioaffecting molecule.

Thus, the reaction of the X-region of the present crosslinkers with a carbonyl or hemiacetal functional groups results in the formation of a carbon-nitrogen double bond. When X is H₂N(CH₂)ₙNH—, the linkage is an imine. It may be necessary to stabilize the imine bond, and this may be accomplished by any conventional method, such as reduction. Suitable reducing agents include NaBH$_4$ and Na(CN)BH$_3$.

The present crosslinkers may be coupled to molecules via the Z region by a number of different methods. For example, when Z is 2- or 4-dithiopyridyl, the crosslinker may be coupled directly to molecules which contain a free mercapto group via a disulfide exchange reaction. The progress of the coupling may be monitored by detecting the liberated pyridine-thione.

Alternatively, the crosslinker where Z is a dithiopyridyl may be reacted with a molecule which possesses a disulfide group in the presence of a reducing agent, such as NaBH$_4$ or dithiothreitol (DTT). The disulfide group of the molecule to be coupled with the crosslinker may be created by first linking the molecule to be coupled to another molecule which contains a disulfide group. For example, a molecule may be first coupled to TPCH or SPDP via the X region or succinimidyl group, respectively, to obtain a molecule with a dithiopyridyl group, and then reacted with another molecule already derivatived with one of the present crosslinkers where Z is dithiopyridyl in the presence of a reducing agent.

In another embodiment, either a free thiol group originating from Z=thiolacetate or from the reduction of Z=thiopyridyl may be reacted with a molecule which contains either a disulfide group, maleimide group, or halide, such as iodide or bromide. Again, the disulfide group on the molecule to be coupled to the present crosslinker may be created by first reacting the molecule to be coupled with a disulfide-containing molecule, such as TPCH or SPDP. In addition, when the Z-region of the crosslinker is maleimide, the crosslinker may be linked to molecules which contain a free sulfhydryl group by direct reaction to form a sulfide or with molecules which contain a disulfide group by reaction in the presence of a reducing agent.

The present crosslinkers exhibit numerous advantages over those of the prior art. In particular, the NH$_2$-containing reactive groups of X permit the site-specific labelling of biomolecules and bioaffecting molecules. In particular, the present crosslinkers can be used to form site-specific labelled antibodies which retain a high degree of binding.

For example, TPCH can be linked to human IgM antibody 1688 which has had its carbohydrate region oxidized by either mild periodate or enzymatic oxidation. Derivatization of the antibody with as many as 35 TPCH crosslinker molecules did not affect antibody binding to the tumor antigen. In contrast, the introduction of only 16 SPDP molecules per IgM antibody resulted in virtually a complete loss of the antibody binding function.

Further, when approximately four cobra venom factor molecules were coupled to antibody 1688 via TPCH, the antigen binding function decreased by less than a factor of 1.5. On the other hand, coupling about the same number of cobra venom molecules via SPDP to antibody 1688 resulted in a decrease in antibody binding function by a factor of 40. These data demonstrate that the novel site-specific heterobifunctional crosslinking reagents of the present invention permit the synthesis of immunoconjugates with unimpaired antigen binding capabilities.

The present crosslinkers are also efficiently and rapidly incorporated into biomolecules such as antibodies. For example, FIG. 1 compares the degree of incorporation of TPCH and the structurally most similar crosslinker from Japanese Patent Application J63-57569, S-(2-thiopyridyl)-mercaptopropionic acid hydrazide (TPMPH), into human monoclonal IgM antibody 1688 under two different coupling conditions. In both cases, TPCH is incorporated into the antibody in a significantly greater amount.

FIG. 2 shows the rates of incorporation of TPCH and TPMPH into human monoclonal IgM antibody 1688 under identical coupling conditions. The results presented in FIG. 2 demonstrate that the incorporation of comparable amounts of crosslinker molecules per antibody requires approximately a 3-fold increase in time for TPMPH as compared for TPCH. Consequently, the use of TPCH permits a reduction in the exposure of the antibody to the oxidizing agent, in this case sodium periodate. As noted above extended exposure of the antibody to the oxidizing agent produces undesired side reactions of the primary amino groups of the antibody with the generated aldehyde residues and decreases the antigen binding capability. Since the use of TPCH reduces the time that the antibody is exposed to the oxidizing agent, it reduces the amount of undesired side reactions and ensures high antibody binding activity.

In addition, the water solubility of TPCH is significantly higher than that of TPMPH. In distilled water TPCH can be easily dissolved to a concentration of 1M (5mg of TPCH (14.2 μmoles)/14.2 μl), whereas the maximum solubility of TPMPH is 150 mM (5mg of TPMPH (2.1 μmoles)/145 μl).

In another embodiment, the present invention relates to biomolecules which have already been coupled to the present crosslinkers. Any of the previously mentioned biomolecules may be derivatized with the present functional groups. Antibodies are the preferred molecules to be linked by the present crosslinkers, and human monoclonal IgM antibody 1688 is particularly preferred.

Since the sulfhydryl groups of the Z portion of the present crosslinkers are protected, the present crosslinkers are stable and can be stored and thereby are useful reagents for kits. The present crosslinkers may be contained in a kit in either a completely unreacted form or already attached to a molecule via the X group. The exact contents of a particular kit will vary depending on the intended use and whether the crosslinker is attached to a molecule, and if so, the nature of the attached molecule.

All publications cited herein are incorporated herein by reference.

Other features of the invention will become apparent in the course of the following descriptions of exemplary embodiments which are given for illustration of the invention and are not intended to be limiting thereof.

EXAMPLES

Preparation of
N,N'-di-(tert-Butyloxycarbonyl)-L-Cystine Dihydrazide

A solution of 2.47 g (5.28 mmol) of N,N'-di(tert-butyloxycarbonyl)-L-cystine dimethyl ester in 50 ml methanol was treated dropwise with 10 ml anhydrous hydrazine at room temperature. The solution was maintained at room temperature for two hours over which time a fine white material precipitated. The solution was cooled to 0° C. for 30 minutes and the product was collected by filtration and washed with ice-cold methanol to provide 2.14 g (86.8%) of white crystals. $^1$H NMR (CD$_3$COCD$_3$): 9.0 (br s, 1H, exchangeable with D$_2$O), 5.62 (br d, 1H, exchangeable with D$_2$O), 4.84 (m, 1H), 3.5 (br, 1H, exchangeable with D$_2$O), 2.92 (br, 2H), 1.45 (s, 9H).

Preparation of Tetra-(tert-Butyloxycarbonyl)-L-Cystine Dihydrazide

A suspension of 10.40 g (22.22 mmol) of N,N'-di(tert-butyloxycarbonyl)-L-cystine dihydrazide in 180 ml ethanol was treated with 20 ml diisopropylethylamine and warmed to reflux. The suspension dissolved upon warming, and 9.70 g (44.44 mmol) of di-(tert-butyl)dicarbonate was added portionwise. The clear, colorless solution was refluxed for thirty minutes and then allowed to cool to room temperature. After 20 minutes the product began to crystallize from solution. The mixture was stored at room temperature for one hour, then cooled to 0° C. for one hour. The white crystalline product was collected by filtration and was washed with ice-cold ethanol. 10.80 g (72.8%) were obtained. $^1$HNMR was very complex due to the apparent restricted rotation about the three amide-type bonds. At least three rotamers can be identified in the spectrum.

Preparation of Di-(tert-Butyloxycarbonyl)-L-Cysteine Hydrazide

Zinc dust (3 g) was added in portions over two hours to a suspension of 10.80 g (16.17 mmol) tetra(tert-butyloxycarbonyl)-L-cystine dihydrazide in 40 ml acetic acid containing 6 ml water. Gradually the suspension dissolved and after two hours the solution was concentrated under reduced pressure, and the residue was partitioned between methylene chloride and saturated aqueous sodium bicarbonate. The methylene chloride was dried over sodium sulfate and concentrated to a viscous glass. The yield was 10.0 g (92.6%). $^1$H NMR was very complex due to the apparent restricted rotation about the three amide-type bonds. At least three rotamers can be identified in the spectrum.

Preparation of Di-(tert-Butyloxycarbonyl)-S-(2-Thiopyridyl)-L-Cysteine Hydrazide 6.57 g (29.85 mmol) of 2,2'-dipyridyl disulfide was added portionwise to a solution of 5.00 g (14.93 mmol) di-(tert-butyloxycarbonyl)-L-cysteine hydrazide in 75 ml methanol at room temperature. This solution was maintained at room temperature for 24 hour, then concentrated in vacuo to a yellow syrup. The crude product was taken up in 400 ml methanol and 20 g silica gel (32–60 µm) was added. The crude product was absorbed onto the silica gel by evaporation of the solvent, and the impregnated gel was placed atop a 95 mm i.d. × 55 mm column of silica gel (32–60 µm). The product was isolated by eluting with 35 ethyl acetate: 65 hexanes. Fractions (100 ml each) containing product were pooled and concentrated to provide 3.5 g (52.8%) of a colorless glass. $^1$H NMR (CDCl$_3$) was complex due to the presence of at least two rotamers in solution: 9.54 (br, 0.25H, exchangeable with D$_2$O), 8.60 (br, 0.75H, exchangeable with D$_2$O), 6.553 (br, 1H, exchangeable with D$_2$O), 5.786 (m, 0.5H), 4.925 (m, 0.5H), 4.526 (br s, 1H), 3.384 (m, 1H), 2.910 (m, 1H), 1.456 (br s, 9H), 1.408 (br, 9H).

Preparation of S-(2-Thiopyridyl)-L-Cysteine Hydrazide Trihydrochloride (TPCH) A solution of 1.15 g (2.58 mmol) of di(tert-butyloxycarbonyl)-S-(2-thiopyridyl)-L-cysteine hydrazide in 15 ml ethyl acetate was cooled to 0° C. and 25 ml of a saturated solution of anhydrous hydrogen chloride in ethyl acetate was added slowly. After 30 minutes a white crystalline material began to separate. The mixture was stirred at room temperature for 4 hours, then filtered under argon, and washed with ethyl acetate, and dried under argon, then under vacuum to provide 830 mg (91%) of hygroscopic white crystals. $^1$H NMR (D$_2$O): 8.63 (m, 1H), 8.31 (m, 1H), 8.14 (m, 1H), 7.74 (m, 1H), 4.47 (m, 1H), 3.45 (m, 2H) ppm. $^{13}$C NMR (DMSO-d$_6$) 166, 157, 149, 140, 122, 121, 50, 21 ppm.

Derivatization of Antibody with TPCH

Human IgM (2.5 mg) in 0.1M sodium acetate, pH 5.5 (1 mg IgM/ml) was oxidized in the presence of 10.7 mg (50 µmoles) NaIO$_4$ and 7 mg (19.8 µmoles) of TPCH. After 20 minutes at 0° C. the reaction mixture was chromatographed on a Sephadex G-25 column to remove access NaIO$_4$ and uncoupled TPCH. The derivatized IgM molecules were eluted with 0.1M sodium phosphate, 0.1M sodium chloride, pH 7.5, and stored at 4° C. The extent of modification was determined to be 17 TPCH molecules per IgM by monitoring the release of pyridine-2-thione at 343 nm during incubation of the derivatized antibody in the presence of 10 mM dithiothreitol as described in J. Carlsson, H. Drevin, and R. Axen, *Biochem. J.*, vol. 173, pp. 723–737 (1978), which is incorporated herein by reference.

Conjugation of SPDP-Derivatized Cobra Venom Factor With TPCH-Derivatized IgM Antibody Cobra venom factor (CVF) was derivatized with 2 molecules of N-succinimidyl-3-(2-pyridyldithio)propionate (SPDP) per CVF molecule as described in E. C. Petrella, S. D. Wilkie, C. A. Smith, A. C. Morgan, Jr., and C.-W. Vogel, *J. Immunol. Meth.*, vol. 104, pp. 159–172 (1987), which is incorporated herein by reference. After removal of excess SPDP by size exclusion chromatography the modified CVF was incubated in 0.1M sodium acetate, 0.1M sodium chloride, pH 4.5, containing 50 mM dithiothreitol to generate free sulfhydryl residues. After 20 minutes at 25° C., dithiothreitol was removed by size exclusion chromatography and 1.85 mg of free sulfhydryl-containing CVF was incubated with 1 mg of TPCH-derivatized IgM at a final protein concentration of 1.25 mg/ml in 0.1M sodium phosphate, 0.1M sodium chloride, pH 7.5, at 25° C. After 24 hours free cobra venom factor was removed by size exclusion chromatography on a TSK-4000 HPLC column. The immunoconjugate fraction contained IgM and CVF covalently coupled at a stoichiometry of 1:3.2 as determined by densitometry of the gel electrophoretically separated immunoconjugate fraction.

Derivatization of Antibody with SPDP

Human IgM (2.5 mg) at a concentration of 1 mg/ml in 0.1M sodium phosphate, 0.1M sodium chloride, pH 7.5, was incubated with 8.8 µg of SPDP for 30 minutes at 25° C. The reaction mixture was then chromatographed on a Sephadex G-25 column to remove excess SPDP. The SPDP-modified human IgM was eluted with 0.1M sodium phosphate, 0.1M sodium chloride, pH 7.5, and stored at 4° C. The extent of modification was determined to be 8 SPDP molecules per antibody using the method described above for TPCH derivatization. When human IgM was incubated with 36.7 µg/ml of SPDP for 30 minutes at 25° C., a ratio of 16 SPDP molecules per antibody was obtained.

Conjugation of SPDP-Derivatized Cobra Venom Factor to SPDP-Derivatized IgM Antibody The conjugation was carried out under identical conditions as described above for TPCH-derivatized antibody. Using human IgM derivatized with 8 SPDP molecules, the rsulting immunoconjugates contained IgM and CVF at a ratio of 1:5.6.

Comparison of the Binding Function of TPCH- and SPDP-Derivatized IgM Antibody The binding functions of TPCH- and SPDP-derivatized IgM antibodies were determined by a radioimmunoassay. The principle of the assay consists of measuring the ability of an unmodified or modified IgM 1688 antibody to compete for antigen with a radiolabelled (otherwise unmodified) IgM 1688 antibody. The radiolabelled antibody is present in a constant amount, whereas the unlabelled (unmodified or modified) antibody is added in varying amounts. The inhibition of the binding of the radiolabelled antibody is measured.

The antigen is obtained from a 20% NH$_4$SO$_4$ precipitate of colon carcinoma cells, WiDr, and coated at a concentration of 8 µg/ml for 15 hours at 4° C. onto polystyrene microtiter plates. The antigen coated wells are blocked with 250 µl of 1% (weight/volume) fish gelatin and phosphate buffer saline (PBS) (pH 7.2) for 1 hour at room temperature, and then washed twice with 0.05% (volume/volume) Tween 20 ®, and 5% (volume/volume) glycerol. Thereafter 50 µl of unlabelled and 50 µl of radiolabelled IgM 1688 antibody in PBS (pH 7.2) containing 1% (weight/volume) bovine serum albumin (BSA) (Buffer A) is added, mixed, and incubated at 4° C. After 15 hours, the wells are washed three times with Buffer A and then counted for radioactivity.

(a) Retention of antigen binding capability after derivatization with 17 TPCH molecules The amount of 1688 IgM required to achieve 50% inhibition in the radioimmunoassay was 4.0 µg/ml for unmodified IgM and 5.5 µg/ml for TPCH-derivatized IgM.

(b) Retention of antigen binding capability after derivatization with 16 and 8 SPDP molecules The amount of 1688 IgM required to achieve 50% inhibition in the radioimmunoassay was 4.0 µg/ml for unmodified IgM and 13.3 µg/ml for IgM derivatized with 8 SPDP molecules. When derivatized with 16 SPDP molecules 50% inhibition could not be achieved even at a concentration to 40 µg/ml of derivatized IgM (12% inhibition).

(c) Retention of antigen binding capability after coupling of 3.2 molecules of CVF to 1688 IgM derivatized with 17 TPCH molecules The amount of IgM in the IgM-CVF conjugates required to achieve 50% inhibition was 6.0 µg/ml.

(d) Retention of antigen binding capability after coupling of 5.6 molecules CVF to 1688 IgM derivatized with 8 SPDP molecules Even at a concentration of 40 µg/ml IgM in the IgM-CVF conjugates not more than 12% inhibition could be achieved.

Efficiency of Incorporation of TPCH and TPMPH into Human IgM in the Presence of 20 mM Sodium Periodate Human IgM (2.5 mg) was oxidized in 1.25 ml of 0.1M sodium acetate, pH 5.5, in the presence of 5.3 mg sodium periodate with either 6.9 mg (20 µmoles) of TPCH trihydrochloride (M.W.=353.5 daltons) or 4.4 mg (20 µmoles) of TPMPH (M.W.=229.3 daltons) at 0° C. Aliquots (250 µl) of the reaction mixture were applied to Sephadex G-25 column chromatography to remove excess sodium periodate and uncoupled TPCH or TPMPH. The derivatized IgM molecules were eluted with 0.1M sodium phosphate, 0.1 M sodium chloride, pH 7.5 The extent of modification was determined as described above.

Efficiency of Incorporation of TPCH and TPMPH into Human IgM in the Presence of 1 mM Sodium Periodate Human IgM (2.5 mg) was oxidized in the presence of 0.27 mg sodium periodate under identical conditions as described above. The extent of derivatization was determined after 20 minutes of incubation using the procedure described above.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. The compound S-(2-thiopyridyl)-L-cysteine hydrazide having the formula:

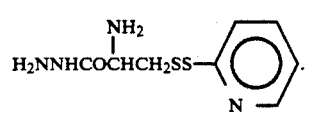

* * * * *

UNITED STATES PATENT AND TRADEMARK OFFICE
CERTIFICATE OF CORRECTION

PATENT NO. : 5,157,123

DATED : October 20, 1992

INVENTOR(S) : Jane J. Zara et al

It is certified that error appears in the above-identified patent and that said Letters Patent is hereby corrected as shown below:

Column 3, line 20, change "688" to --1688--;

line 22, change "TPMP" to --TPMPH--.

Column 4, line 10, change "$OP_3$-" to --$PO_3$- --;

line 33, change "$HO_2CCH_2CH2N$..." to $HO_2CCH_2CH_2N$...--.

Column 6, line 25, change "Y-aminobutyric" to --γ-aminobutyric--.

Column 7, line 59, change

"Uses of the Crosslinkers invention may be used to
              couple a variety of compounds."

to

--Uses of the Crosslinkers

The heterobifunctional crosslinkers of the present invention may be used to couple a variety of compounds.--

Signed and Sealed this

Eighteenth Day of January, 1994

Attest:

BRUCE LEHMAN

Attesting Officer      Commissioner of Patents and Trademarks